(12) United States Patent
Zhang et al.

(10) Patent No.: US 11,872,377 B2
(45) Date of Patent: Jan. 16, 2024

(54) SYRINGE

(71) Applicant: GUANGDONG HAIOU MEDICAL APPARATUS CO., LTD., Puning (CN)

(72) Inventors: Zhuoxuan Zhang, Puning (CN); Jiangsheng Zhang, Puning (CN)

(73) Assignee: GUANGDONG HAIOU MEDICAL APPARATUS CO., LTD., Puning (CN)

( * ) Notice: Subject to any disclaimer, the term of this patent is extended or adjusted under 35 U.S.C. 154(b) by 450 days.

(21) Appl. No.: 17/134,161

(22) Filed: Dec. 24, 2020

(65) Prior Publication Data
US 2021/0113770 A1 Apr. 22, 2021

Related U.S. Application Data

(63) Continuation of application No. PCT/CN2019/102577, filed on Aug. 26, 2019.

(30) Foreign Application Priority Data

Sep. 6, 2018 (CN) .......................... 201811038848.8

(51) Int. Cl.
*A61M 5/31* (2006.01)
*A61M 5/315* (2006.01)
(Continued)

(52) U.S. Cl.
CPC ...... *A61M 5/3129* (2013.01); *A61M 5/31511* (2013.01); *A61M 5/322* (2013.01); *A61M 5/34* (2013.01)

(58) Field of Classification Search
CPC ...... A61M 5/3129; A61M 5/322; A61M 5/34; A61M 5/50
See application file for complete search history.

(56) References Cited

U.S. PATENT DOCUMENTS

| 5,328,475 A | * | 7/1994 | Chen | ..................... | A61M 5/322 |
| | | | | | 604/110 |
| 6,093,171 A | * | 7/2000 | Huang | ................... | A61M 5/322 |
| | | | | | 604/110 |

(Continued)

FOREIGN PATENT DOCUMENTS

| CN | 1512899 A | 7/2004 |
| CN | 1705496 A | 12/2005 |

(Continued)

OTHER PUBLICATIONS

International Search Report for PCT/CN2019/102577, dated Nov. 11, 2019.

*Primary Examiner* — Bradley J Osinski

(57) ABSTRACT

A syringe, comprising: a barrel, comprising a needle accommodating-cavity and a plunger accommodating-cavity; a pull-back element, accommodated in the needle accommodating-cavity, wherein a needle is mounted on the pull-back element; a plunger, disposed in the plunger accommodating-cavity and movable between pushed-in and pulled-out position, wherein a head portion of the plunger enters the cavity of the pull-back element proximate to the plunger accommodating-cavity and is engaged therein in the pushed-in position; a biasing force structure, disposed in the cavity of the pull-back element and/or the head portion of the plunger, wherein the head portion of applies a biasing force on the pull-back element through the biasing force structure, and when the head portion is moved to the pulled-out position, the biasing force structure causes the pull-back element and the needle to tilt with respect to the axis of the barrel through the biasing force.

19 Claims, 6 Drawing Sheets

(51) Int. Cl.
*A61M 5/34* (2006.01)
*A61M 5/32* (2006.01)

(56) References Cited

U.S. PATENT DOCUMENTS

| | | | |
|---|---|---|---|
| 6,342,045 B1 * | 1/2002 | Somers | A61M 5/322 604/218 |
| 2007/0078390 A1 | 4/2007 | Cing-hong | |
| 2011/0092913 A1 | 4/2011 | Fang | |

FOREIGN PATENT DOCUMENTS

| | | |
|---|---|---|
| CN | 1795021 A | 6/2006 |
| CN | 201194970 Y | 2/2009 |
| CN | 202105275 U | 1/2012 |
| CN | 103285466 A | 9/2013 |
| CN | 209392504 U | 9/2019 |

* cited by examiner

SYRINGE

TRAVERSE REFERENCE TO RELATED PRESENT DISCLOSURE PROGRAMS

The present application is a continuation-application of International Application PCT/CN2019/102577, with an international filing date of Aug. 26, 2019, the contents of all of which are hereby incorporated by reference.

BACKGROUND

1. Technical Field

The present disclosure relates to medical device technology, and particularly to a syringe.

2. Description of Related Art

Syringes are common and widely used medical devices, mainly used for liquid medicine or blood test. In recent years, the use of disposable sterile syringes has been promoted to avoid repeated use and cross-infection. However, the existing disposable sterile syringes remain intact after being used up and can be reused, which gives some criminals opportunities to take advantage of the used syringes, bringing potential for cross-infection and the spread of disease.

In the prior art, there is one kind of retractable self-destructing syringes, which includes a needle, a needle-holder, a barrel and a push rod. The needle is installed on the needle-holder, and the needle-holder is installed on the drug outlet end of the barrel. The lower part of the push rod, which is located in the barrel, is equipped with a rubber plug. The lower end of the push rod is provided with a barb fixing part that penetrates the rubber plug. The barb fixing part is fixed with an upwardly opening spring barb. And the upper end of the needle-holder is provided with a clamping inner cavity for fixing with the spring barb.

In the above prior art, after the syringe is used, the spring barb and the clamping inner cavity on the needle-holder are firmly locked together to realize the self-destruction of the syringe. But if the clamping inner cavity and the spring barb are damaged, the needle part may still be pushed out and used again, causing the risk of disease transmission.

BRIEF DESCRIPTION OF THE DRAWINGS

To describe the technical schemes in the embodiments of the present disclosure or in the prior art more clearly, the following briefly introduces the drawings required for describing the embodiments or the prior art. It should be understood that, the drawings in the following description merely show some embodiments of the present disclosure. For those skilled in the art, other drawings can be obtained according to the drawings without creative efforts.

In which.

DETAILED DESCRIPTION

Figure 1:
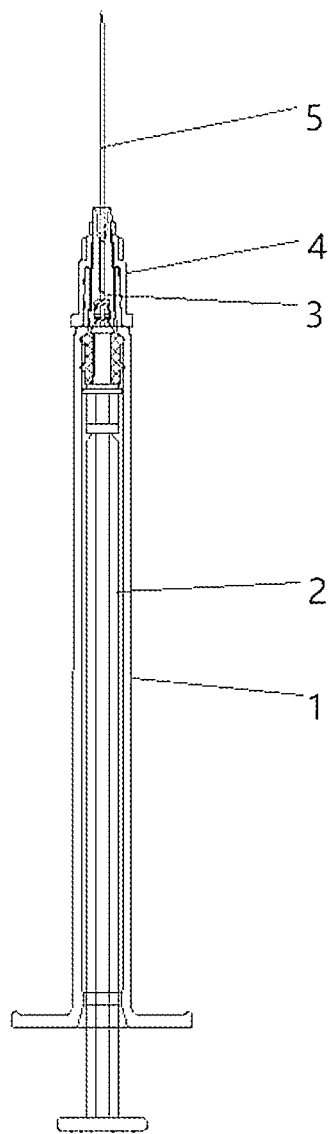
FIG. 1 is a schematic structural diagram of a syringe according to the first embodiment of the present disclosure.

The technical solutions in the embodiments of the present disclosure will be clearly and completely described below in conjunction with the drawings in the embodiments of the present disclosure. Apparently, the following embodiments are only part of the embodiments of the present disclosure, not all of the embodiments of the present disclosure. All other embodiments obtained by those skilled in the art without creative efforts are within the scope of the present disclosure.

It should be noted that in the description of the present disclosure, the terms "center", "upper", "lower", "left", "right", "vertical", "horizontal", "inner", "outer", etc. that indicate orientation or positional relationship are based on the orientation or positional relationship shown in the drawings. Those terms are only for the convenience of describing the present disclosure and simplifying the description, rather than indicating or implying that the related device or element must have a specific orientation or be constructed or used in a specific orientation, and therefore cannot be understood as a limitation to the present disclosure. In addition, the terms "first", "second", and "third" are only used for descriptive purposes, and cannot be understood as indicating or implying relative importance.

In the description of the present disclosure, it should be noted that the terms "install", "engage" and "connect" should be understood in a broad sense, unless otherwise clearly specified and limited. For example, it can be a fixed connection or a detachable connection or a one-piece connection. It can be a mechanical connection or an electrical connection. It can be a direct connection or an indirect connection through an intermediate medium, or an internal communication between two components. For those of ordinary skill in the art, the specific meanings of the above-mentioned terms in the present disclosure can be understood in specific situations.

In addition, the technical features involved in the different embodiments of the present disclosure described below can be combined with each other as long as there is no conflict between them.

Figure 2:
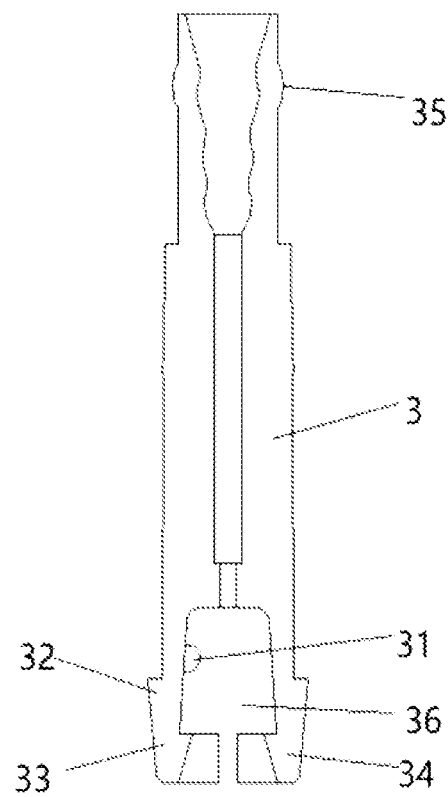
FIG. 2 is a schematic structural diagram of the structure of the pull-back element of FIG. 1.
Figure 3:
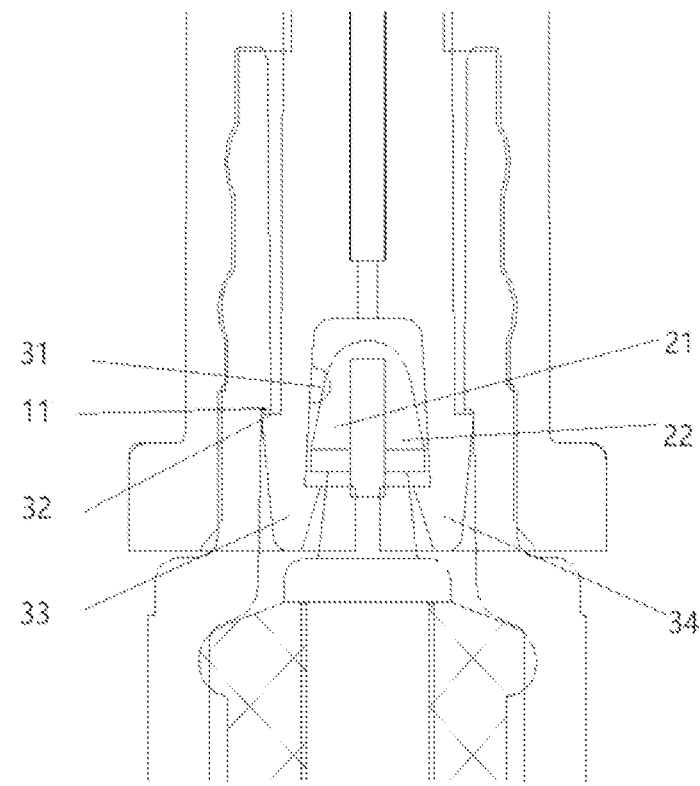
FIG. 3 is an enlarged view of a partial structure of the syringe of FIG. 1.
Figure 4:
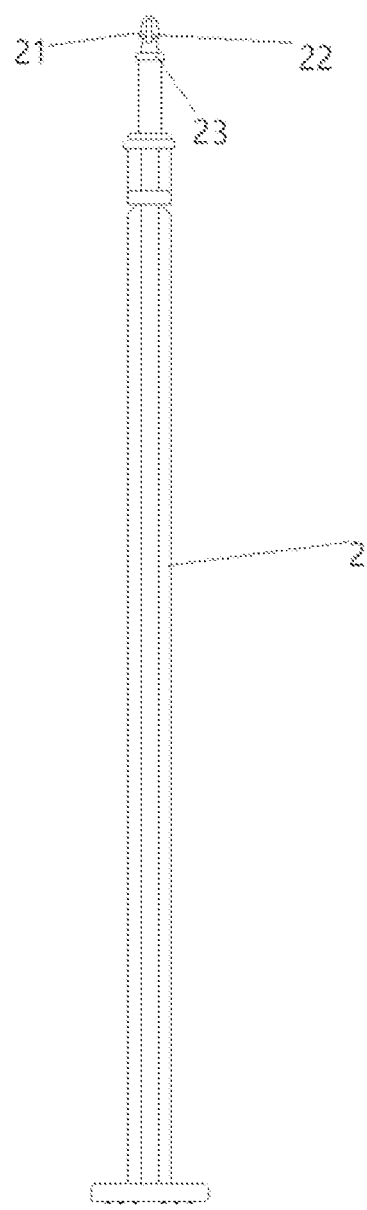
FIG. 4 is a schematic diagram of the structure of the plunger of FIG. 1.
Figure 5:
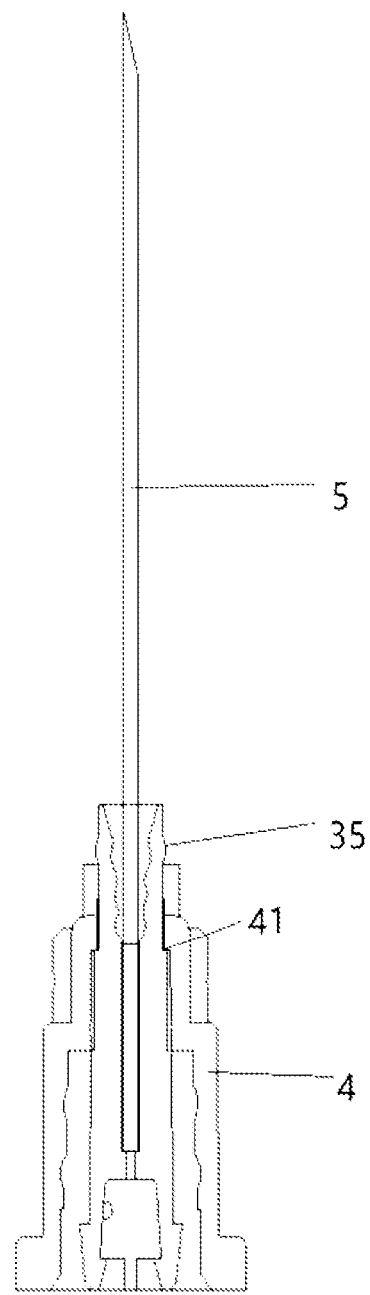
FIG. 5 is an enlarged view of a partial structure of the syringe of FIG. 1.

FIGS. 1-6 show an embodiment of a syringe, which includes a barrel 1, a pull-back element 3, a needle-holder 4, and a plunger 2. The barrel 1 includes a needle accommodating-cavity and a plunger accommodating-cavity, and the cross-sectional area of the needle accommodating-cavity is less than that of the plunger accommodating-cavity. The needle-holder 4 is arranged on the outer side of the first end of the barrel 1. The pull-back element 3 is accommodated in the needle accommodating-cavity, and a needle 5 is mounted on the pull-back element 3. A cavity 36 is provided at an end of the pull-back element 3 proximate to the plunger accommodating-cavity. The needle-holder 4 is connected to the pull-back element 3 in a tight fit. As shown in FIG. 2, the side wall of the cavity 36 of the pull-back element 3 is provided with a first boss 31 as a biasing force structure. The plunger 2 is disposed in the plunger accommodating-cavity and movable between a pushed-in position and a pulled-out position. A head portion of the plunger 2 enters the cavity 36 of the pull-back element 3 and is engaged therein when in the pushed-in position. The head portion of the plunger 2 applies a biasing force on the pull-back element 3 by means of the biasing force structure, and when the head portion of the plunger 2 is moved to the pulled-out position, the biasing force structure causes the pull-back element 3 and the needle 5 to tilt with respect to the axis of the barrel 1 in the plunger accommodating-cavity by means of the biasing force. The first end of the pull-back element 3 is an elastic end, and the cavity 36 is arranged in the elastic end. The size of the open end of the cavity 36 is smaller than that of the head portion of the plunger 2. The head portion of the plunger 2 enters the cavity 36 by squeezing the open end. As shown in FIG. 3, the first end of the pull-back element 3 includes a first elastic end 33 and a second elastic end that are parallel to each other. A gap is provided between the first elastic end 33 and the second elastic end 34. The head portion of the plunger 2 is a conical elastic portion, and below the elastic portion is a limiting portion 23 fixedly connected to the elastic portion. The limiting portion 23 is able to prevent the plunger 2 from pushing out the needle-holder 4. The elastic portion includes a first semi-cone portion 21 and a second semi-cone portion 22, and a gap is provided between the first semi-cone portion 21 and the second semi-cone portion 22. In order to prevent the pull-back element 3 equipped with the needle 5 from being pushed out due to the excessive pushing force on the plunger 2, the inner wall of the syringe 1 is provided with a first step portion 11 along the circumferential direction to prevent the pull-back element 3 from moving toward the first end of the barrel 1. The outer wall of the pull-back element 3 is provided with a second step portion 32 engaging with the first step portion 11 along the circumferential direction. In order to prevent the reaction force generated during the puncture of the needle 5 from causing the pull-back element 3 to return to the syringe 1, as shown in FIG. 5, the pull-back element 3 is provided with a second boss 35 at the upper end of the needle-holder 4. The top end of the needle-holder 4 is arranged adjacent to the lower end of the second boss 35 for blocking the movement of the pull-back element 3 towards the interior of the barrel 1 under the force of the needle 5. A sealing ring 41 is sleeved and fixed on the pull-back element 3 where the needle-holder and the pull-back element are tight-fitting connected, and the sealing ring 41 is used to seal the gap between the needle-holder 4 and the pull-back element 3. In this embodiment, the second boss 35 is arc-shaped in its cross-sectional view, which facilitates the smooth retract of the pull-back element 3 into the syringe 1 after the injection is completed, driven by the plunger 2.

Figure 6:
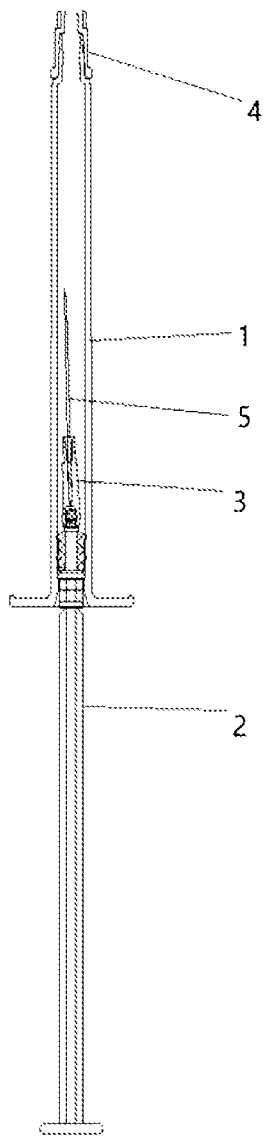
FIG. 6 is a structural schematic diagram of the syringe of FIG. 1 in a pulled-back state after use.

When the syringe is in use, before the injection is completed, the pull-back element 3 is kept in a position where its axis is in the same line as the axis of the barrel 1 under the supporting force of the barrel 1 and the needle-holder 4. During the injection, the plunger 2 is pushed toward the first end of the barrel 1 under the action of external force. When the head portion of the plunger 2 enters the open end of the cavity 36, the first semi-cone portion 21 and the second semi-cone portion 22 of the head portion of the plunger 2 are squeezed and contracted, and can smoothly enter the cavity 36. After the head portion of the plunger 2 is completely inserted, the first semi-cone portion 21 and the second semi-cone portion 22 lose the compression and return to the original state. Since the first end of the pull-back element 3 includes a first elastic end 33 and a second elastic end 34 parallel to each other, a gap is provided between the first elastic end 33 and the second elastic end 34. When the head portion of the plunger 2 enters, the first elastic end 33 and the second elastic end 34 are squeezed to increase the distance between them, thus allowing the head portion of the plunger 2 to enter smoothly. After the head portion of the plunger 2 enters, the first elastic end 33 and the second elastic end 34 return to their original state. Since the size of the open end of the cavity 36 is smaller than that of the head portion of the plunger 2, after entering the cavity 36, the head portion of the plunger 2 cannot exit from the cavity 36, thus achieving locking between the head portion of the plunger 2 and the pull-back element 3. After the injection is completed, the plunger 2 is pulled back. Since the head portion of the plunger 2 has been locked with the pull-back element 3, the pull-back element 3 moves back with the plunger 2. As shown in FIG. 6, after the pull-back element 3 loses the support force of the needle-holder 4 and the barrel 1, the head portion of the plunger 2 squeezes the first boss 31 on the side wall of the cavity 36, the pull-back element 3 deflects, and the needle 5 deflects with the pull-back element, such that the needle 5 is prevented from being pushed out of the barrel 1 again, which eliminates the risk of spreading diseases and improves safety during use.

In an alternative embodiment, the biasing force structure is a protrusion arranged on the head portion of the plunger 2 and deviated from the center of the head portion, as long as it can ensure that the head portion of the plunger 2 can smoothly enter the cavity 36 of the pull-back element 3, and the head portion of the plunger 2 can generate a biasing force on the pull-back element 3 to offset the axis of the pull-back element 3 from the axis of the barrel 1.

In an alternative embodiment, the first end of the pull-back element 3 can be divided into more than two elastic ends, with gaps between the plurality of elastic ends.

The technical features of the above-mentioned embodiments can be arbitrarily combined. For the sake of brevity of description, the descriptions do not include all possible combinations of the technical features in the above-mentioned embodiments. However, the combination of these technical features will be considered to be within the scope described in this specification as long as there is no contradiction.

The above-mentioned embodiments are merely illustrative of several embodiments of the present disclosure. Although the description is specific and detailed, it should not to be comprehended as limiting the scope of the present disclosure. It should be noted that, for those skilled in the art, a number of variations and improvements can still be made without departing from the spirit and scope of the present disclosure. Therefore, the scope of the present disclosure should be determined by the appended claims.

LIST OF THE REFERENCE SIGNS 1 barrel
2 plunger
3 pull-back element
4 needle-holder
5 needle
11 first step portion
21 first semi-cone portion
22 second semi-cone portion
23 limiting portion
31 first boss
32 second step portion
33 first elastic end
34 second elastic end
35 second boss
36 cavity
41 sealing ring

What is claimed is:
1. A syringe, comprising:
a barrel, comprising a needle accommodating-cavity and a plunger accommodating-cavity, the cross-sectional area of the needle accommodating-cavity being less than that of the plunger accommodating-cavity;
a pull-back element, accommodated in the needle accommodating-cavity, wherein a needle is mounted on the pull-back element, and a cavity is provided at an end of the pull-back element proximate to the plunger accommodating-cavity;
a plunger, disposed in the plunger accommodating-cavity and movable between a pushed-in position and a pulled-out position, wherein a head portion of the plunger enters the cavity of the pull-back element and is engaged therein when in the pushed-in position;
a biasing force structure, provided in the cavity of the pull-back element and/or the head portion of the plunger, wherein the head portion of plunger applies a biasing force on the pull-back element by means of the biasing force structure, and when the head portion of the plunger moves to the pulled-out position, the biasing force structure causes the pull-back element and the needle to tilt with respect to the axis of the barrel in the plunger accommodating-cavity by means of the biasing force;
wherein an inner wall of the syringe is provided with a first step portion along the circumferential direction to prevent the pull-back element from moving toward a first end of the barrel, and an outer wall of the pull-back element is provided with a second step portion engaging with the first step portion along the circumferential direction, and
wherein the syringe further comprises a needle-holder arranged on an outer side of the first end of the barrel, and the needle-holder is in a tight-fitting connection with the pull-back element, wherein a sealing ring is sleeved and fixed on the pull-back element where the needle-holder and the pull-back element are tight-fitting connected.

2. The syringe of claim 1, wherein the biasing force structure is a first boss provided on the side wall of the cavity of the pull-back element.

3. The syringe of claim 2, wherein a first end of the pull-back element is an elastic end, and the cavity is arranged in the elastic end, wherein the size of the open end of the cavity is smaller than that of the head portion of the plunger, and the head portion of the plunger enters the cavity by squeezing the open end.

4. The syringe of claim 3, wherein the first end of the pull-back element comprises a first elastic end and a second elastic end that are parallel to each other, and a gap is provided between the first elastic end and the second elastic end.

5. The syringe of claim 3, wherein the head portion of the plunger is a conical elastic portion, and a limiting portion fixedly connected to the elastic portion is provided below the elastic portion.

6. The syringe of claim 5, wherein the elastic portion comprises a first semi-cone portion and a second semi-cone portion, and a gap is provided between the first semi-cone portion and the second semi-cone portion.

7. The syringe of claim 1, wherein the biasing force structure is a protrusion provided on the head portion of the plunger and deviated from the center of the head portion.

8. The syringe of claim 1, wherein the pull-back element is provided with a second boss at an upper end of the needle-holder, and a top end of the needle-holder is arranged adjacent to a lower end of the second boss for blocking the movement of the pull-back element towards the interior of the barrel under the force of the needle.

9. The syringe of claim 8, wherein the second boss is arc-shaped in its cross-sectional view.

10. A syringe, comprising:
a barrel comprising a needle accommodating-cavity and a plunger accommodating-cavity, the cross-sectional area of the needle accommodating-cavity being less than that of the plunger accommodating-cavity;
a pull-back element accommodated in the needle accommodating-cavity, wherein a needle is mounted on the pull-back element, and a cavity is provided at an end of the pull-back element proximate to the plunger accommodating-cavity;
a plunger disposed in the plunger accommodating-cavity and movable between a pushed-in position and a pulled-out position, wherein a head portion of the plunger enters the cavity of the pull-back element and is engaged therein when in the pushed-in position;
a biasing force structure provided in the cavity of the pull-back element and/or the head portion of the plunger, wherein the head portion of applies a biasing force on the pull-back element by means of the biasing force structure, and when the head portion of the plunger moves to the pulled-out position, the biasing force structure causes the pull-back element and the needle to tilt with respect to the axis of the barrel in the plunger accommodating-cavity by means of the biasing force,
a needle-holder arranged on an outer side of the first end of the barrel, and the needle-holder is in a tight-fitting connection with the pull-back element;
a sealing ring is sleeved and fixed on the pull-back element where the needle-holder and the pull-back element are tight-fitting connected.

11. The syringe of claim 10, wherein the biasing force structure is a first boss provided on the side wall of the cavity of the pull-back element.

12. The syringe of claim 11, wherein a first end of the pull-back element is an elastic end, and the cavity is arranged in the elastic end, wherein the size of the open end of the cavity is smaller than that of the head portion of the plunger, and the head portion of the plunger enters the cavity by squeezing the open end.

13. The syringe of claim 12, wherein the first end of the pull-back element comprises a first elastic end and a second elastic end that are parallel to each other, and a gap is provided between the first elastic end and the second elastic end.

14. The syringe of claim 12, wherein the head portion of the plunger is a conical elastic portion, and a limiting portion fixedly connected to the elastic portion is provided below the elastic portion.

15. The syringe of claim 14, wherein the elastic portion comprises a first semi-cone portion and a second semi-cone portion, and a gap is provided between the first semi-cone portion and the second semi-cone portion.

16. The syringe of claim 10, wherein the biasing force structure is a protrusion provided on the head portion of the plunger and deviated from the center of the head portion.

17. The syringe of claim 10, wherein an inner wall of the syringe is provided with a first step portion along the circumferential direction to prevent the pull-back element from moving toward a first end of the barrel, and an outer wall of the pull-back element is provided with a second step portion engaging with the first step portion along the circumferential direction.

18. The syringe of claim 12, wherein the pull-back element is provided with a second boss at an upper end of the needle-holder, and a top end of the needle-holder is arranged adjacent to a lower end of the second boss for blocking the movement of the pull-back element towards the interior of the barrel under the force of the needle.

19. The syringe of claim 18, wherein the second boss is arc-shaped in its cross-sectional view.

* * * * *